(12) United States Patent
Lu et al.

(10) Patent No.: US 11,897,863 B2
(45) Date of Patent: Feb. 13, 2024

(54) INDAZOLE AMINE DERIVATIVE, PREPARATION METHOD THEREFOR AND MEDICAL USE THEREOF

(71) Applicant: ZHEJIANG HISUN PHARMACEUTICAL CO., LTD., Zhejiang (CN)

(72) Inventors: Yongping Lu, Zhejiang (CN); Cheng Ye, Zhejiang (CN); Wenjian Qian, Zhejiang (CN); Taishan Hu, Zhejiang (CN); Lei Chen, Zhejiang (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 578 days.

(21) Appl. No.: 17/267,771

(22) PCT Filed: Aug. 15, 2019

(86) PCT No.: PCT/CN2019/100760
§ 371 (c)(1),
(2) Date: Feb. 10, 2021

(87) PCT Pub. No.: WO2020/035019
PCT Pub. Date: Feb. 20, 2020

(65) Prior Publication Data
US 2021/0309636 A1 Oct. 7, 2021

(30) Foreign Application Priority Data

Aug. 17, 2018 (CN) .......................... 201810937427.2

(51) Int. Cl.
*C07D 401/12* (2006.01)
*C07D 401/14* (2006.01)
(52) U.S. Cl.
CPC ......... *C07D 401/12* (2013.01); *C07D 401/14* (2013.01)
(58) Field of Classification Search
None
See application file for complete search history.

(56) References Cited

U.S. PATENT DOCUMENTS

| 10,160,753 B2 | 12/2018 | Gummadi et al. |
| 10,308,634 B2 | 6/2019 | Bothe et al. |
| 10,435,396 B2 | 10/2019 | Bothe et al. |
| 2019/0071432 A1* | 3/2019 | Bothe ....................... A61P 3/06 |

FOREIGN PATENT DOCUMENTS

| CN | 106458982 A | 2/2017 |
| CN | 107406416 A | 11/2017 |
| WO | 2007115058 A2 | 10/2007 |
| WO | 2015104662 A1 | 7/2015 |
| WO | 2015193846 A1 | 12/2015 |
| WO | 2016083433 A1 | 6/2016 |
| WO | 2017009798 A1 | 1/2017 |
| WO | 2017108744 A1 | 6/2017 |
| WO | 2017148902 A1 | 9/2017 |

OTHER PUBLICATIONS

International Search Report for International Application No. PCT/CN2019/100760, dated Nov. 25, 2019, 7 pages.

* cited by examiner

*Primary Examiner* — Joseph R Kosack
*Assistant Examiner* — Quincy Andre McKoy
(74) *Attorney, Agent, or Firm* — Armstrong Teasdale LLP

(57) ABSTRACT

Indazole derivatives represented by formula (I) or stereoisomers, tautomers, and pharmaceutically acceptable salts thereof are provided. A preparation method of indazole derivatives represented by formula (I) and a method of use of the indazole derivatives as therapeutic agents is also provided. The indazole derivatives of formula (I) are especially useful as interleukin-1 receptor-associated kinase 4 (IRAK4) inhibitors

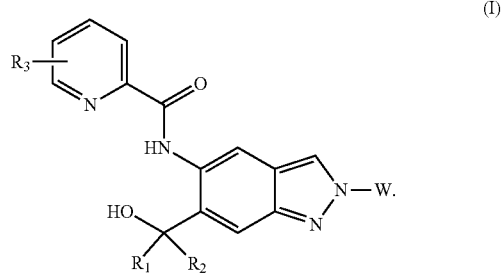

(I)

18 Claims, No Drawings

INDAZOLE AMINE DERIVATIVE, PREPARATION METHOD THEREFOR AND MEDICAL USE THEREOF

CROSS-REFERENCE TO RELATED APPLICATIONS

This application is a U.S. National Phase Application of PCT/CN2019/100760, filed Aug. 15, 2019, which claims the benefit of priority to CN Application No. 201810937427.2, filed Aug. 17, 2018, the contents of which are hereby expressly incorporated by reference in their entirety.

TECHNICAL FIELD

The invention relates to novel indazole amines derivatives, a preparation method thereof, a pharmaceutical composition comprising the derivatives and use thereof as a therapeutic agent, in particular as an IRAK4 inhibitor.

BACKGROUND

Interleukin-1 receptor-associated kinase 4 (IRAK-4) is a member of IRAK family of intracellular serine-threonine kinases. The kinase family also includes other members, such as IRAK-1, IRAK-2 and IRAK-M. IRAK-M is only expressed in monocytes and macrophages, while IRAK-1, IRAK-2 and IRAK-4 are universally expressed. IRAK-4 is mainly composed of N-terminal conserved dead domain (DD), hinge domain and C-terminal central kinase domain (KD). DD is the domain where IRAK-4 binds to the primary response gene 88 (MyD88) of adaptor protein myeloid differentiation factor. KD is composed of 12 sub-domains and has typical characteristics of serine-threonine kinase domain. The main function of IRAK-4 is to phosphorylate its substrate through KD, and then activate downstream signal molecules. IRAK-4 is a key factor downstream of the inflammatory signal transduction pathway mediated by interleukin-1 receptor (IL-1R)/Toll-like receptor (TLR), and plays a key role in the immune system. When interleukin-1 receptor (IL-1R) or Toll-like receptor (TLR) binds to ligand, IRAK4 can mediate signal transmission and activate the expression of downstream inflammatory factors. TLR can receive ligand signals from the interaction between organism and microorganism or the stimulation of endogenous substances, as well as the first wave of inflammatory signals and innate immune response signals caused by these stimulations. TLR plays a very important role in many diseases including infection, autoinflammatory diseases and many other human diseases. As tumor necrosis factor-α (TNF-α) and other major cytokines, interleukin-1 (IL-1) is a key factor in inflammation-mediated pathway, which can transmit and amplify signals. Because the signal pathways mediated by TLR, IL-1R and other cytokine receptors are inter-related, IRAK4, the key signal factor in the inflammatory pathway of TLR and IL-1R, plays an important role in systemic inflammatory response, and can be used as an effective potential target for treating various inflammation-related diseases.

Although many IRAK4 inhibitors have been reported in the literature, there are no drugs targeting this target available in the market. Only PF-06650833 by Pfizer, BAY-1834845 by Bayer and CA-4948 by Aurigene have entered the clinical stage. In the Phase I clinical results reported by Pfizer, PF-06650833 adopts sustained-release dosage form, which not only limits its application, but also increases the cost for developing drugs. BAY-1834845 by Bayer and CA-4948 by Aurigene have not been reported for clinical trials results.

IRAK4 inhibitors based on indazole skeleton have been widely studied.

WO2016083433 discloses indazole derivatives, in which the 2-position is alkyl which is substituted by halogen, haloalkyl, halocycloalkyl, hydroxyl, sulfoxide group, sulfone group, or four to six-membered heterocycloalkyl containing oxygen, sulfur, sulfoxide group or sulfone group, rather than amino alkyl, lactam group or nitrogen-containing aromatic heterocyclic ring group. WO2017148902 discloses that the substituent at 2-position is a nitrogen-containing five-membered or six-membered saturated heterocycle group, rather than azetidinyl, aminoalkyl, lactam group or nitrogen-containing aromatic heterocyclic ring group.

WO2015104662 discloses indazole derivatives substituted at 2-position by alkyl and cycloalkyl, wherein the alkyl and cycloalkyl can be substituted by halogen, hydroxyl, alkoxy, hydroxyalkyl, haloalkyl and haloalkoxy, rather than aminoalkyl, azacycloalkyl, lactam group or nitrogen-containing aromatic heterocyclic ring group. WO2015193846 discloses indazole derivatives substituted at 2-position by methyl or cyclopropyl.

WO201709798 reports indazole derivatives represented by the following general formula:

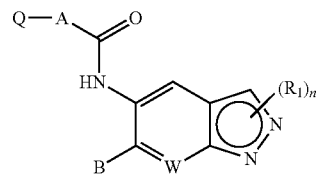

wherein, examples disclose indazole derivatives substituted at 2-position by piperidinyl (Example 54), morpholinyl (Example 55) and N-methyl piperidinyl (Example 56). However, the substituents at 6-position of the indazole derivatives in the above three examples are all cyclopropyl and no indazole derivatives substituted at 6-position by dialkyl benzyl alcohol group are disclosed. The efficacy, safety, applicability, solubility and the like of the compounds and experimental drugs disclosed in the prior art are still unsatisfactory, so there is a need to research and develop new inhibitors of interleukin-1 receptor-associated kinase 4 (IRAK4) so as to meet the increasing medical and health needs of people.

SUMMARY OF THE INVENTION

By screening a large number of compounds, the inventors of the present invention unexpectedly found that the compound represented by the following formula (I) has good inhibitory effects on IRAK4 kinase activity and/or solubility.

Therefore, in the first aspect, the present invention provides indazolamine derivatives represented by formula (I) or stereoisomers, tautomers or pharmaceutically acceptable salts thereof:

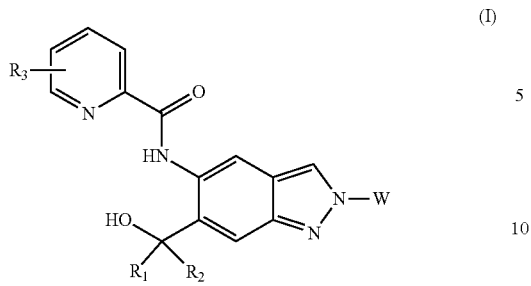

(I)

wherein:
- R₁ and R₂ are independently selected from hydrogen or C₁-C₆ alkyl;
- R₃ is selected from halogen, cyano, carboxyl, —CONR$^A$R$^B$, haloalkyl or heteroaryl; wherein the heteroaryl is optionally further substituted by one or more substituents selected from halogen, hydroxyl, cyano, carboxyl, —CONR$^A$R$^B$ or haloalkyl;
- W is azetidinyl, nitrogen-containing aromatic heterocyclic ring group or nitrogen-containing aromatic heterocyclic ring group bonded via a single methylene group; wherein the azetidinyl is optionally further substituted by one or more substituents selected from —COR$^C$, —SO₂R$^D$, C₁-C₆ alkyl or C₃-C₆ cycloalkyl; wherein the nitrogen-containing aromatic heterocyclic ring group is optionally further substituted by one or more substituents selected from halogen, cyano, carboxyl, —CONR$^A$R$^B$ and haloalkyl;
- or, W has a structure of formula (II):

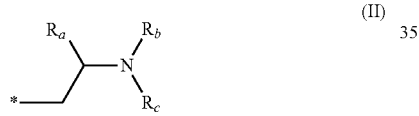

(II)

* represents the bonding site of the group to the rest of the molecule;
- R$_a$ is selected from hydrogen, C₁-C₆ alkyl or C₃-C₆ cycloalkyl; wherein the C₁-C₆ alkyl or C₃-C₆ cycloalkyl is optionally further substituted by one or more substituents selected from halogen, hydroxyl, carboxyl and —SO₂NR$^E$R$^F$;
- R$_b$ and R$_c$ are independently selected from hydrogen, —COR$^C$, —SO₂R$^D$, C₁-C₆ alkyl or C₃-C₆ cycloalkyl; or, any two of R$_a$, R$_b$ and R$_c$ together with the atom to which they are attached may form a 4-8 membered nitrogen-containing heterocyclic ring, wherein the nitrogen-containing heterocyclic ring may be further substituted by one or more oxo groups (O=);
- R$^A$, R$^B$, R$^E$ and R$^F$ are independently selected from hydrogen, C₁-C₆ alkyl or C₃-C₆ cycloalkyl; wherein the alkyl or cycloalkyl is optionally further substituted by one or more substituents selected from halogen, hydroxyl, cyano or haloalkyl;
- R$^C$ and R$^D$ are independently selected from C₁-C₆ alkyl or C₃-C₆ cycloalkyl; wherein the alkyl or cycloalkyl is optionally further substituted by one or more substituents selected from halogen, hydroxyl, cyano or haloalkyl.

In some preferred embodiments of the present invention, the compounds of formula (I) or stereoisomers, tautomers or pharmaceutically acceptable salts thereof have the structure of formula (III):

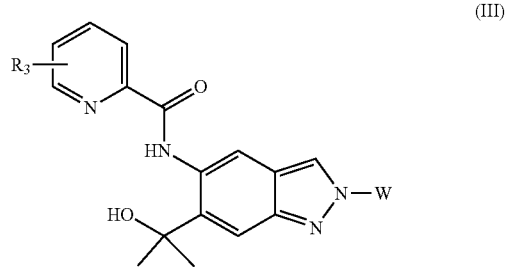

(III)

wherein, R₃ and W are defined as in formula (I).

In some preferred embodiments of the present invention, the compounds of formula (I) or (II) or stereoisomers, tautomers or pharmaceutically acceptable salts thereof have the structure of formula (IV):

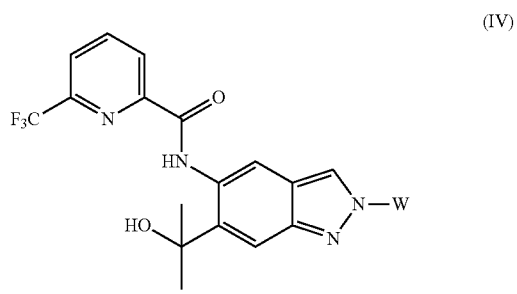

(IV)

wherein, W is defined as in formula (I).

In some preferred embodiments of the present invention, the compounds of formula (I), (II) or (IV), or stereoisomers, tautomers or pharmaceutically acceptable salts thereof have the structure of formula (Va), (Vb) and (Vc):

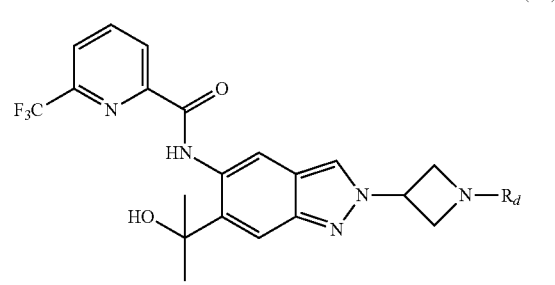

(Va)

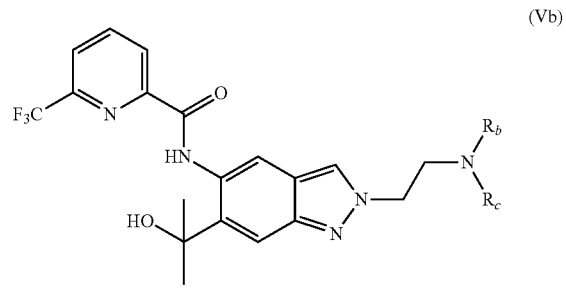

(Vb)

-continued

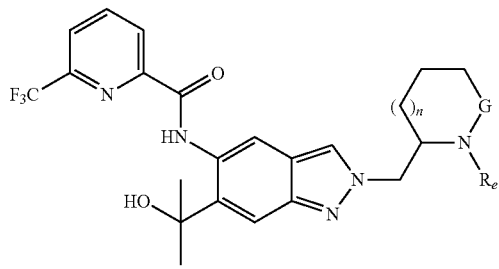

(Vc)

wherein:
R$_b$ and R$_c$ are defined as in formula (I);
R$_d$ and R$_e$ are independently selected from hydrogen, —COR$^C$, —SO$_2$R$^D$, C$_1$-C$_6$ alkyl or C$_3$-C$_6$ cycloalkyl; wherein, R$^C$ and R$^D$ are as defined in formula (I);
G is selected from —CH$_2$—, —CO— or —SO$_2$—;
n is an integer from 0 to 2.

In some preferred embodiments of the present invention, the compounds of formula (I), (II), (IV), (Va), (Vb) or (Vc), or stereoisomers, tautomers or pharmaceutically acceptable salts thereof are selected from:

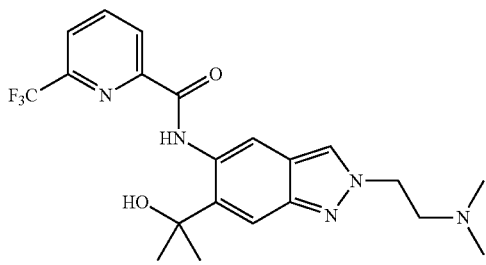

1

N-(2-(2-(dimethylamino)ethyl)-6-(2-hydroxypropan-2-yl)-2H-indazol-5-yl)-6-(trifluoromethyl)pyridin-2-carboxamide;

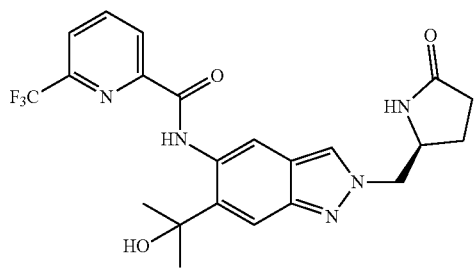

2

(S)—N-(6-(2-hydroxypropan-2-yl)-2-((5-oxopyrrolidin-2-yl)methyl)-2H-indazol-5-yl)-6-(trifluoromethyl)pyridin-2-carboxamide;

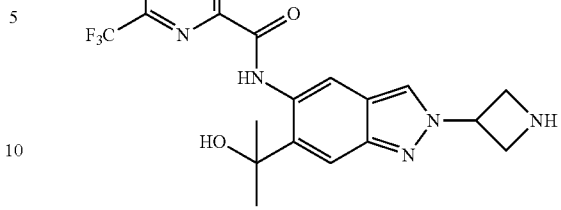

3

N-(2-(azetidin-3-yl)-6-(2-hydroxypropan-2-yl)-2H-indazol-5-yl)-6-(trifluoromethyl)pyridin-2-carboxamide.

Further, the present invention provides a pharmaceutical composition comprising a therapeutically effective amount of the compounds of formula (I), (II), (IV), (Va), (Vb) or (Vc), or stereoisomers, tautomers or pharmaceutically acceptable salts thereof, and optional pharmaceutically acceptable carriers, excipients or combinations thereof.

In another aspect, the present invention provides use of the compounds of formula (I), (II), (IV), (Va), (Vb) or (Vc), or stereoisomers, tautomers or pharmaceutically acceptable salts thereof, the composition comprising the the compounds, or stereoisomers, tautomers or pharmaceutically acceptable salts thereof in preparation of a medicament for inhibiting IRAK4 kinase activity.

In yet another aspect, the present invention provides use of compounds of formula (I), (II), (IV), (Va), (Vb) or (Vc), or stereoisomers, tautomers or pharmaceutically acceptable salts thereof, or pharmaceutical composition comprising the compound or stereoisomers, tautomers or pharmaceutically acceptable salts thereof in preparation of a medicament for preventing or treating autoimmune diseases, inflammatory diseases or cancers, wherein the autoimmune diseases, inflammatory diseases or cancers are preferably selected from lymphoma, endometriosis, psoriasis, lupus erythematosus, multiple sclerosis or rheumatoid arthritis; wherein the lymphoma is preferably primary central nervous system lymphoma or diffuse large B-cell lymphoma with MYD88 L265P mutation.

The present invention further provides a method for inhibiting IRAK4 kinase activity, the method comprises administering the compounds of formula (I), (II), (IV), (Va), (Vb) or (Vc), or stereoisomers, tautomers or pharmaceutically acceptable salts thereof, or the pharmaceutical composition comprising the compounds, or stereoisomers, tautomers or pharmaceutically acceptable salts thereof.

The present invention further provides a method for preventing or treating autoimmune diseases, inflammatory diseases or cancers, the method comprises administering the compounds of formula (I), (II), (IV), (Va), (Vb) or (Vc), or stereoisomers, tautomers or pharmaceutically acceptable salts thereof, or the pharmaceutical composition comprising the compounds, or stereoisomers, tautomers or pharmaceutically acceptable salts thereof to a subject in need thereof. The autoimmune diseases, inflammatory diseases or cancers are preferably selected from lymphoma, endometriosis, psoriasis, lupus erythematosus, multiple sclerosis or rheumatoid arthritis; wherein the lymphoma is preferably primary central nervous system lymphoma or diffuse large B-cell lymphoma with MYD88 L265P mutation.

The present invention further provides the compounds of formula (I), (II), (IV), (Va), (Vb) or (Vc), or stereoisomers, tautomers or pharmaceutically acceptable salts thereof, or the pharmaceutical composition comprising the compound, or stereoisomers, tautomers or pharmaceutically acceptable salts thereof, for use as a medicament.

The present invention also provides the compound of formula (I), (II), (IV), (Va), (Vb) or (Vc), or stereoisomers, tautomers or pharmaceutically acceptable salts thereof, the composition comprising the compound, or stereoisomers, tautomers or pharmaceutically acceptable salts thereof, for use in a method of inhibiting IRAK4 kinase or for use as inhibitor of IRAK4 kinase.

The present invention further provides the compounds of formula (I), (II), (IV), (Va), (Vb) or (Vc), or stereoisomers, tautomers or pharmaceutically acceptable salts thereof, or the pharmaceutical composition comprising the compounds, or stereoisomers, tautomers or pharmaceutically acceptable salts thereof, for use in a method for preventing or treating autoimmune diseases, inflammatory diseases or cancers. Wherein, the autoimmune diseases, inflammatory diseases or cancers are preferably selected from lymphoma, endometriosis, psoriasis, lupus erythematosus, multiple sclerosis or rheumatoid arthritis; wherein the lymphoma is preferably primary central nervous system lymphoma or diffuse large B-cell lymphoma with MYD88 L265P mutation.

Some terms used in the specification and claims of the present invention are defined as follows:

"Alkyl", when taken as a group or a part of a group, refers to a linear or branched aliphatic hydrocarbon group. It is preferably a $C_1$-$C_{20}$ (e.g., C1, C2, C3, C4, C5, C6, C10, C15, etc.) alkyl, and more preferably a $C_1$-$C_6$ (e.g., C1, C2, C3, C4, C5 or C6) alkyl. Examples of alkyl include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-di methylbutyl, 2-ethylbutyl, 2-methylpentyl, 3-methylpentyl, 4-methylpentyl, 2,3-dimethylbutyl, etc. The alkyl may be substituted or unsubstituted.

"Cycloalkyl" refers to saturated or partially saturated monocyclic, condensed, bridged and spirocyclic carbocycle. It is preferably $C_3$-$C_{12}$ (e.g., C3, C4, C5, C6, C7, C8, C9, C10, C11, C12) cycloalkyl, more preferably $C_3$-$C_8$ cycloalkyl, and most preferably $C_3$-$C_6$ cycloalkyl. Examples of monocyclic cycloalkyl include, but are not limited to, cyclopropyl, cyclobutyl, cyclopentyl, cyclopentenyl, cyclohexyl, cyclohexenyl, cyclohexadienyl, cycloheptyl, cyclohepttrienyl, cyclooctyl, etc., and is preferably cyclopropyl and cyclohexyl.

"Halogen" refers to fluorine, chlorine, bromine or iodine.

"Haloalkyl" refers to alkyl substituted by halogen, wherein the halogen and the alkyl are as specified herein. It is preferably $C_1$-$C_6$ haloalkyl. Examples of haloalkyl include, but are not limited to, monofluoromethyl, difluoromethyl, trifluoromethyl, pentafluoroethyl, etc.

"Methylene" refers to a group of —CH$_2$—.

"Oxo" refers to the O= group.

"Heteroaryl" refers to 5 or 6-membered monocyclic aromatic hydrocarbon group, 9 or 10-membered bicyclic aromatic hydrocarbon group containing at least one (e.g., 1, 2, 3, 4 or 5) heteroatom (0, S or N), and examples thereof include, but are not limited to, thienyl, furyl, pyrrolyl, thiazolyl, oxazolyl, imidazolyl, pyrazolyl, pyridyl, quinolyl, isoxazole, etc.

"Nitrogen-containing heterocyclic ring" refers to a structure in which at least one ring-carbon atom in the cycloalkyl is replaced by nitrogen atoms (for example, 1, 2, 3, 4 or 5 nitrogen atoms), and the rest ring-atoms are independently selected from carbon, oxygen and sulfur atoms, wherein the cycloalkyl is defined as above, and 4 to 8-membered ring is preferred. Examples thereof include, but are not limited to, tetrahydropyrrolyl, piperidinyl, morpholinyl, nitromethylpiperidyl, etc.

"Nitrogen-containing aromatic heterocyclic ring" refers to an aromatic ring structure containing 5 to 6 ring-atoms, wherein at least one ring-atom (for example, 1, 2, 3, 4 or 5) is nitrogen, and the rest ring-atoms are independently selected from carbon, oxygen and sulfur. Examples thereof include, but are not limited to, pyrrolyl, thiazolyl, oxazolyl, imidazolyl, pyrazolyl, pyridyl, etc.

EMBODIMENTS

Examples are intended to show the preparation of representative compounds represented by formula (I) and related structural characterization data. It shall be noted that the following examples are only used to illustrate the present invention and not to limit the present invention. $^1$H NMR chemical shift is expressed in ppm, wherein s=single peak, d=double peak, t=triple peak, m=multiple peak and br=broadened. If the coupling constant is provided, its unit is Hz. Unless otherwise specified, the raw materials used for synthesis of the compounds of the present invention are all commercially available or derived from the synthetic routes of known reference documents. The manufacturers of commercially available reagents are Shanghai Bide Pharmaceutical Technology Co., Ltd., Shanghai Shaoyuan Reagent Co., Ltd., Shanghai Lingkai Pharmaceutical Technology Co., Ltd., Nanjing Yaoshi Technology Co., Ltd., and Shanghai Haohong Biomedical Technology Co., Ltd. Iodo-pyroglutamol was synthesized by referring to WO2007115058.

The following abbreviations are used in the invention:

HATU: O-(7-azabenzotriazol-1-yl)-N,N,N',N'-tetramethyluronium hexafluorophosphate DIEA: N,N-diisopropyl ethylamine DMF: N,N-dimethyl formamide

EXAMPLE 1

N-(2-(2-(dimethylamino)ethyl)-6-(2-hydroxypropan-2-yl)-2H-indazol-5-yl)-6-(trifluoromethyl)pyridin-2-carboxamide

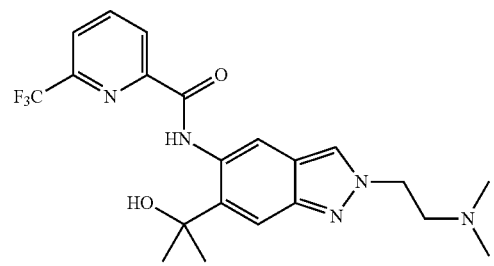

Step 1: Synthesis of Methyl 5-nitro-2H-indazol-6-carboxylate

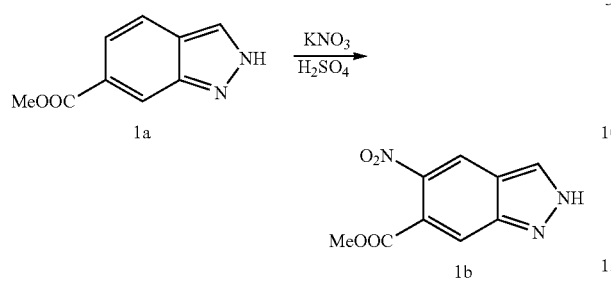

Compound 1a (22 g, 125 mmol) was taken and dissolved in 200 mL concentrated sulfuric acid in ice bath. Potassium nitrate (15.15 g, 1.2 eq) was slowly added thereto, and the obtained mixture was reacted at room temperature. TLC was used to monitor the reaction until the compound 1a was completely reacted. The obtained product was precipitated by pouring the reaction solution into crushed ice, filtered, washed with water and dried in vacuum at ° C. for 8 h to obtain compound 1b (25 g, 90%).

Step 2: Synthesis of Methyl 5-amino-2H-indazol-6-carboxylate

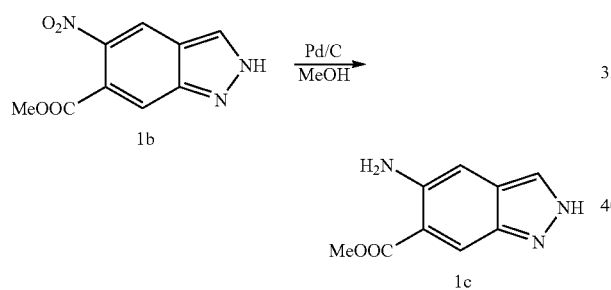

The compound 1b (10.72 g, 48 mmol) and Pd/C (2.2 g, 20 wt %) were taken, and 500 mL of methanol was added thereto as solvent. Then the mixture was pumped down and filled with hydrogen by a hydrogen balloon, which was repeated for three times. The mixture was stirred at 30° C., and TLC was used to monitor the reaction until the compound 1b was completely reacted. The obtained product was filtered with diatomite/silica gel and concentrated to obtain compound 1c (9.02 g, 67%), which was directly used for the next synthesis.

Step 3: Synthesis of Methyl 5-(6-(trifluoromethyl)pyridin-2-carboxamide)-2H-indazol-6-carboxylate

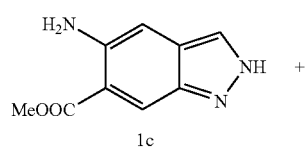 +

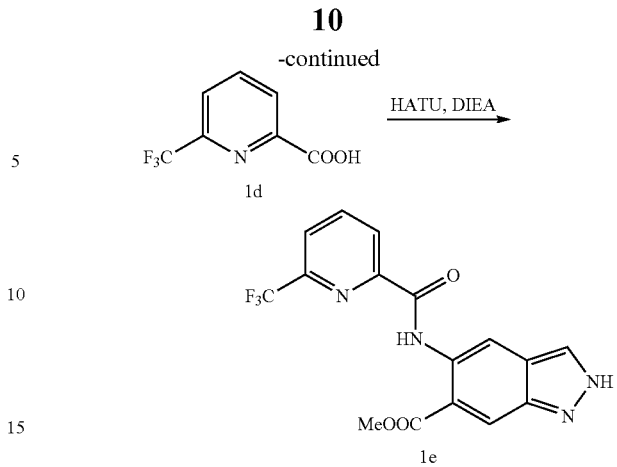

Compound 1d (4.99 g, 1.1 eq), 30 mL of dichloromethane, HATU (11.91 g, 1.2 eq) and DIEA (3.58 g, 1.2 eq) were added into the reaction flask, stirred at room temperature for 30 min, then the compound 1c (4.5 g, 22.3 mmol) was added thereto, and reacted overnight at room temperature. TLC was used to monitor the reaction until the compound 1c was completely reacted. The obtained solution was washed with saturated aqueous solution of sodium bicarbonate (30 mL×2), dried over anhydrous sodium sulfate, separated with silica gel column chromatography by eluting with ethyl acetate/n-hexane to obtain compound 1e (8.03 g, 92%).

Step 4: Synthesis of N-(6-(2-hydroxypropan-2-yl)-2H-indazol-5-yl)-6-(trifluoromethyl)pyridin-2-carboxamide

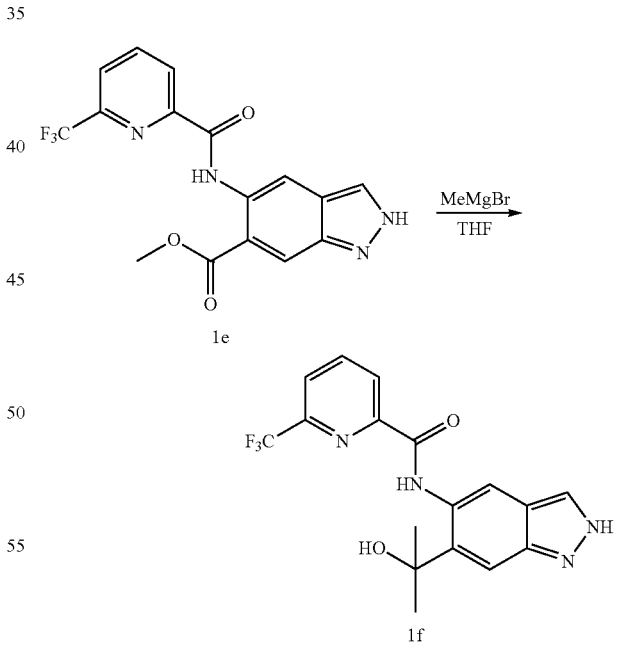

The compound 1e (4.0 g, 11 mmol) was added into reaction flask, dissolved with 50 mL of anhydrous tetrahydrofuran. Under ice bath, MeMgBr (1.0M, 50 mL) was dropwisely slowly added into the reaction flask and reacted overnight at room temperature, then MeMgBr (50 mL) added thereto. After the compound 1e was completely reacted, the reaction solution was quenched by adding saturated aqueous solution of ammonium chloride, extracted with ethyl acetate, dried over anhydrous sodium sulfate and separated with silica gel column chromatography by eluting with methanol/dichloromethane to obtain compound 1f (c2.33 g, 58%).

Step 5: Synthesis of N-(2-(2-(dimethylamino)ethyl)-6-(2-hydroxypropan-2-yl)-2H-indazol-5-yl)-6-(trifluoromethyl)pyridin-2-carboxamide

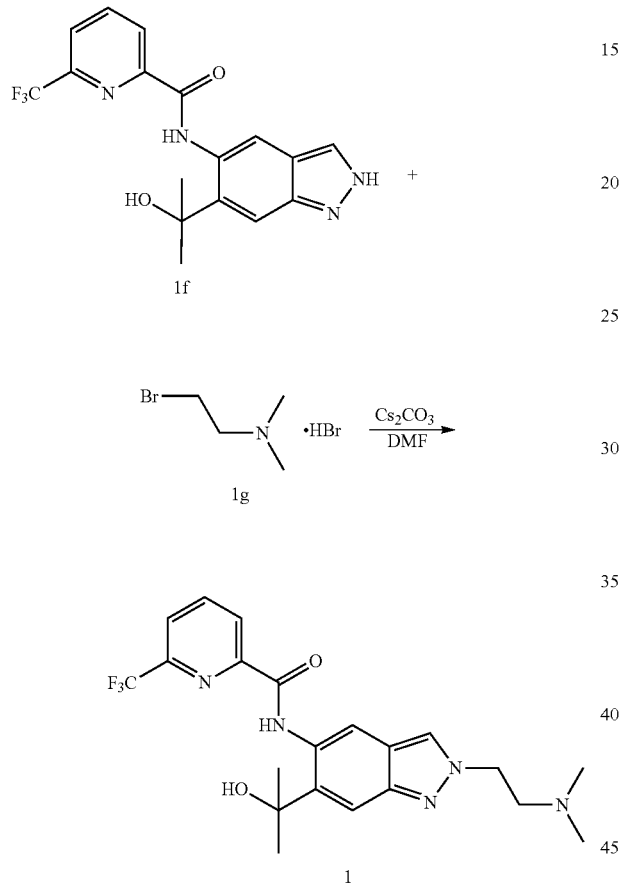

The compound 1f (0.25 g, 0.7 mmol) was taken and dissolved in 5 mL of DMF, and cesium carbonate (1.34 g, 6 eq) was added thereto. The obtained mixture was stirred for 30 min at room temperature, then 1 g (0.49 g, 3 eq) was added thereto, and reacted overnight at room temperature. TLC was used to monitor the reaction until the compound 1f was completely reacted. Thus obtained mixture was washed with 20 ml of saturated brine, extracted with ethyl acetate twice (20 mL×2), dried over anhydrous sodium sulfate, filtered, concentrated under reduce pressure, separated by preparative column with gradient elution of 1% elutant A (water+0.1% formic acid) and 99% elutant B (acetonitrile) at 0.8 mL/min to obtain compound 1 (100 mg, 33%).

LCMS m/z (ESI): 436.5[M+H]$^+$ $^1$H NMR (400 MHz, DMSO-d$_6$) δ 12.36 (s, 1H), 8.71 (s, 1H), 8.46 (d, J=7.8 Hz, 1H), 8.38 (d, J=7.8 Hz, 1H), 8.15 (d, J=7.8 Hz, 1H), 7.57 (s, 1H), 5.96 (s, 1H), 4.50 (t, J=6.2 Hz, 2H), 2.80 (t, J=6.2 Hz, 2H), 2.19 (s, 6H), 1.62 (s, 6H).

EXAMPLE 2

(S)—N-(6-(2-hydroxypropan-2-yl)-2-((5-oxopyrrolidin-2-yl)methyl)-2H-indazol-5-yl)-6-(trifluoromethyl)pyridin-2-carboxamide

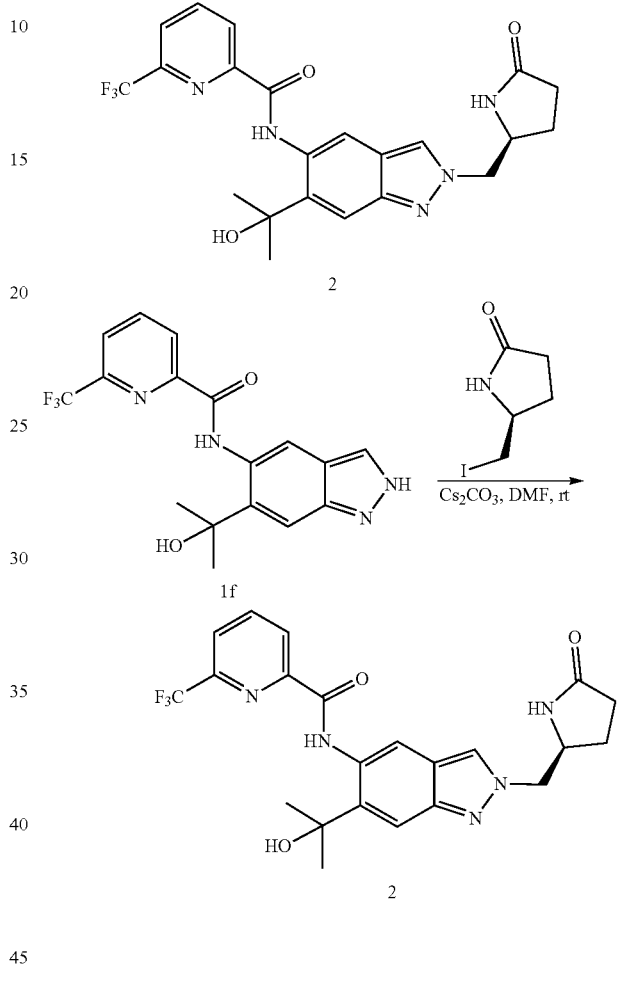

Compound 1f (60 mg, 0.16 mmol), iodo-pyroglutamol (111 mg, 0.49 mmol), cesium carbonate (160 mg, 0.49 mmol), and 5 mL of DMF as solvent were added into reaction flask and reacted at room temperature. TLC was used to monitor the reaction until the compound 1f was completely reacted. 10 ml of saturated brine was added to the reaction mixture and the resultant mixture was extracted with ethyl acetate twice (15 mL×2). The organic phase was washed with saturated brine (10 mL×3) to remove DMF, dried over anhydrous sodium sulfate, filtered, concentrated under reduce pressure, separated by silica gel column by eluting with dichloromethane/methanol to obtain compound 2 (26 mg, 35%).

LCMS m/z (ESI): 462.5[M+H]$^+$ $^1$H NMR (400 MHz, CDCl$_3$) δ 12.28 (s, 1H), 8.78 (s, 1H), 8.46 (d, J=7.8 Hz, 1H), 8.08 (t, J=7.8 Hz, 1H), 7.86 (s, 1H), 7.82 (d, J=7.8 Hz, 1H), 7.60 (s, 1H), 6.68 (s, 1H), 4.48-4.31 (m, 2H), 4.21 (br, 1H), 2.27 (m, 4H), 1.76 (s, 6H).

EXAMPLE 3

N-(2-(azetidin-3-yl)-6-(2-hydroxypropan-2-yl)-2H-indazol-5-yl)-6-(trifluoromethyl)pyridin-2-carboxamide

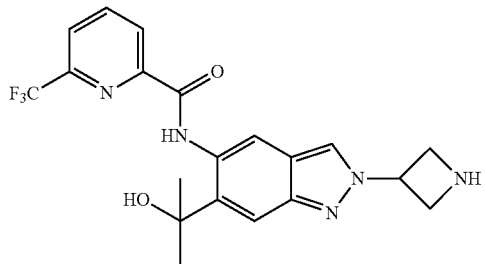

Step 1: Synthesis of 3-(6-(2-hydroxyl propan-2-yl)-5-(6-(trifluoromethyl)pyridin-2-carb oxamide)-2H-indazol-2-yl)azetidin-1-tert-butyl Ester

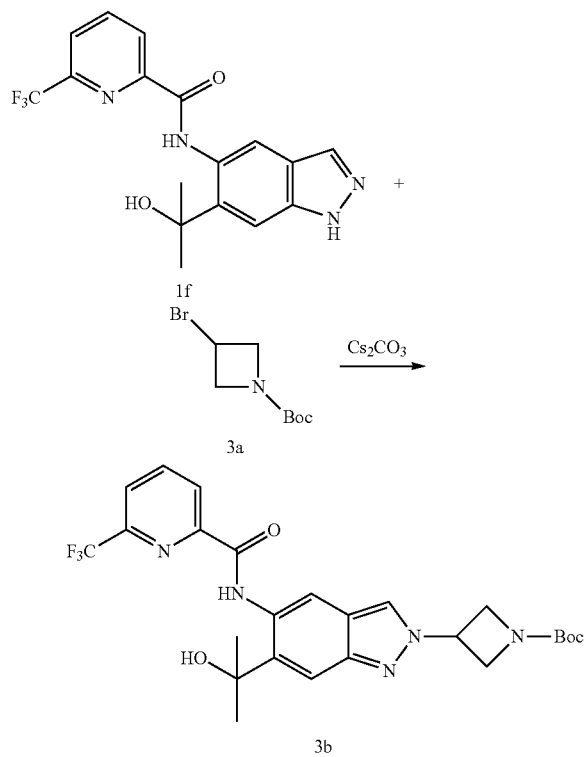

Compound 1f (0.5 g, 1.38 mmol) was taken, dissolved in 2 mL of DMF, and cesium carbonate (1.34 g, 3 eq) was added thereto. The obtained mixture was stirred for 30 min at room temperature, then the compound 3a (0.99 g, 3 eq) was added thereto, and reacted overnight at room temperature. TLC was used to monitor the reaction until the raw materials were completely reacted. Thus obtained mixture was washed with 20 ml of saturated brine, extracted with ethyl acetate twice (30 mL×2), dried over anhydrous sodium sulfate, filtered, concentrated under reduce pressure, separated by silica gel column chromatography by eluting with ethyl acetate/n-hexane (4:1 in volume) to obtain compound 3b (210 mg, 30%).

Step 2: Synthesis of N-(2-(azetidin-3-yl)-6-(2-hydroxypropan-2-yl)-2H-indazol-5-yl)-6-(trifluoromethyl)pyridin-2-carboxamide

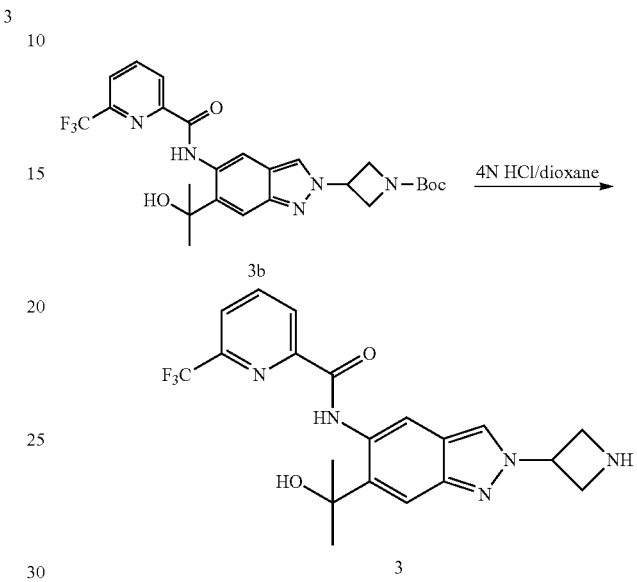

Compound 3b (30 mg, 0.06 mmol) and 2 ml of 4N hydrochloric acid-dioxane solution were added into the reaction tube to react at room temperature. TLC was used to monitor the reaction until the raw material 3b was completely reacted, then 50 ml of ethyl acetate was added thereto. The resultant mixture was washed with saturated aqueous solution of $NaHCO_3$ (10 mL×3), dried over anhydrous sodium sulfate, filtered, concentrated and purified by silica gel column chromatography (MeOH:DCM=1:30) to obtain compound 3 (19 mg, 79%).

LCMS m/z (ESI): 420.1[M+H]$^+$ $^1$H NMR (400 MHz, DMSO-d$_6$) δ 12.36 (s, 1H), 8.71 (s, 1H), 8.45-8.40 (m, 2H), 8.34 (t, J=7.8 Hz, 1H), 8.13 (d, J=7.8 Hz, 1H), 7.59 (s, 1H), 5.97 (br, 1H), 5.49 (m, 1H), 4.10 (t, J=8.0 Hz, 2H), 3.94 (t, J=8.03 Hz, 2H), 1.60 (s, 6H).

Biological Evaluation

Determination of IRAK4 Kinase Activity

The following methods were used to determine the inhibition degree of the preferred compound of the present invention on IRAK4 kinase activity in vitro. In this evaluation, the HTRF®KinEASE-STK S1 Serine/Threonine kinase kit produced by Cisbio was used to determine the phosphorylation degree of biotinylated polypeptide substrate by homogeneous time-resolved fluorescence technique (HTRF).

Detailed methods can be referred to the kit instructions, and the experimental process was briefly described as follows. Firstly, the compounds of the present invention were dissolved in DMSO, and the final concentration was 10 mM. Then, the buffer solution provided in the kit was used for equal gradient dilution, so that the final concentration range of the tested compound in the reaction system was 16000 nM-0.008 nM, and the final concentration of DMSO is less than 2%.

The adenosine triphosphate (ATP) concentration in the test was the corresponding ATP Km value (300 µM) determined in advance. Compounds, kinase, biotinylated polypeptide substrate and ATP were incubated at 37° C. for 1 h for kinase reaction, then anti-phosphorylated Serine/Threonine antibody coupled with compound of europium element and modified XL665 streptavidin were added into the reaction system to terminate the reaction, and incubated at room temperature for 1 h. After incubation, the fluorescence intensity of each well at emission wavelengths of 615 nm and 665 nm was determined on the microplate reader FLUOstar Omega under the excitation wavelength of 337 nm in HTRF mode, and the Ratio value was calculated by using the formula Ratio=(665 nm/615 nm)×$10^4$. Compared with the fluorescence intensity ratio of the control group, the inhibition rates of the compound at each concentration were calculated, and then the IC 50 value of the compound was calculated by fitting the nonlinear curve of logarithmic concentration-inhibition rate with GraphPad Prism5. Results were shown in Table 1 below.

TABLE 1

$IC_{50}$ values of the compound in the present invention for inhibiting IRAK4 kinase activity

| Compound | $IC_{50}$ (nM) |
|---|---|
| 1 | 0.55 nM |
| Control compound BAY-1834845 | 8.6 nM |

Control compound BAY-1834845 (Example 11 of WO2016083433) has structure formula as follows:

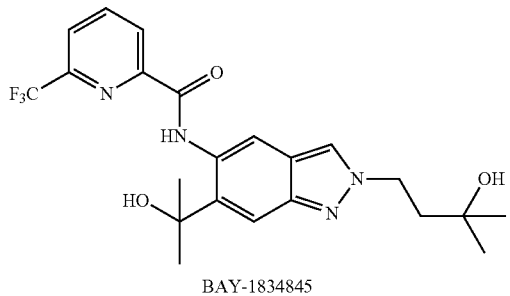 [SMILES: CC(C)(O)CCn1cc2cc(NC(=O)c3cccc(C(F)(F)F)n3)c(C(C)(C)O)cc2n1]

BAY-1834845

Method for Determining THP-1 Cell Activity

The following method was used to determine the ability of the preferred compound of the present invention to inhibit TNF-α (tumor necrosis factor α) secretion in THP-1 cells. TNF-α is a cytokine involved in inflammatory process. In this experiment, TNF-α secretion was triggered by lipopolysaccharide (LPS) incubation.

THP-1 cells were cultured in RPMI 1640 medium supplemented with 10% fetal bovine serum, 1% penicillin/streptomycin, 1% HEPES buffer and 0.05 mM β-mercaptoethanol under the condition of 37° C. and 5% $CO_2$, and the cell concentration should not exceed 1×$10^6$ cells/mL.

A cell suspension containing 150 nM PMA and THP-1 with a F3-F10 generation density of 2.5×$10^5$/mL was distributed to 96 microplates with 200 µL per well. After induced differentiation under the condition of 37° C. and 5% $CO_2$ for 48 h, adherent macrophages were produced. Then PMA supernatant was removed and PBS was used to wash the cells once. In each case, all the drugs were dissolved in 100% DMSO to obtain an initial concentration of 10 mM. The drugs were filtered with 0.22 µm sterile filter membrane before use. LPS was dissolved in PBS with an initial concentration of 1 mg/mL. During use, it was diluted to 20 µg/mL with PBS. Serum-free medium was used to prepare 8 different concentrations of drug with the final concentration of 8000 nM-0.488 nM. 200 µL of drugs were added to each well, and 50 µL of 20 µg/ml LPS (final concentration: 4 µg/mL) was added to each well. They were incubated in a 5% CO 2 incubator at 37° C. for 5 h. The supernatant was collected by centrifugation and stored at −80° C. for later use. As a control, cells were treated with 4 µg/mL LPS and 0.1% DMSO, while in another control group, the wells without cells were treated with 4 µg/mL LPS and 0.1% DMSO.

Determination by using TNF-α ELISA kit: the amount of TNF-α was determined by R&D System Human TNF-α ELISA kit. According to the manufacturer's instructions, 50 µL of RD-1F protein buffer was added to each well, and then 200 µL of standard substance/sample was added to incubate at room temperature for 2 hours. The plate was washed for three times in microplate washer with 300 µL of Wash Buffer per well each time, then 200 µL of TNF-α Conjugate (conjugate of TNF-α antibody and horseradish peroxidase) was added to each well, incubated for 1 h at room temperature, and then washed for three times in microplate washer with 300 µL of Wash Buffer per well each time. 200 µL of Substrate Solution (solution containing hydrogen peroxide and horseradish peroxidase with substrate of diaminobenzidine DAB) was added to each well, and the resultant mixture was incubated in dark for 20 min. 50 µL of Stop Solution (2N sulfuric acid stop solution) was added to each well and evenly mixed, and the absorbance at 450 nm was measured with microplate reader within 30 min. Compared with the fluorescence intensity ratio of the control group, the inhibition rate of the compound at each concentration was calculated, and then the IC 50 value of the compound was calculated by fitting the nonlinear curve of logarithmic concentration-inhibition rate with GraphPad Prism5. Result was shown in Table 2 below.

TABLE 2

$IC_{50}$ value of the compound in the present invention in inhibiting TNF-α secretion in THP-1 cells

| Compound | $IC_{50}$ (nM) |
|---|---|
| 1 | 55 nM |
| Control compound BAY-1834845 | 128 nM |

It can be seen from table 1 that the preferred compound of the present invention has a good inhibitory effect on IRAK4 kinase, and the inhibitory activity IC 50 of Compound 1 on IRAK4 kinase activity is 0.55 nM, which is 15 times higher than that of the control compound BAY-1834845 (Example 11 of WO2016083433). Thus, the compound 1 shows more excellent inhibitory effect on IRAK4 kinase activity.

It can be seen from table 2 that the preferred compound of the present invention also has a good inhibitory effect on TNF-α secretion in THP-1 cells, and its inhibitory effect is twice as high as that of the control compound (55 nM vs 128 nM), which shows significant advantages. Therefore, the compounds of the invention have good prospect to be used as IRAK4 inhibitors and for treating related diseases.

Solubility Test

The following method was used to determine the solubility of the preferred compound of the present invention in phosphate buffer solution (PBS, pH7.4).

1.5 mg of the test compound was taken, and PBS was added thereto to prepare the test solution with theoretical concentration of 2 mg·mL$^{-1}$. The test solution was ultrasonicated for 10 min, and rotated on a rotating tray at room temperature for at least 8 h. After the rotation treatment, the test solution was ultrasonicated for 10 min and centrifuged at 13000 rpm for 15 min. 100 μL of supernatant was transferred to a 0.6 mL new tube for spinning and rinsing for 5 min. 500 μL of supernatant was transferred into the above rinsed 0.6 mL tube. Then the tube was centrifuged at 13000 rpm for 15 min, and the supernatant was taken (or diluted) for analysis by LC-UV. Sample concentration was quantified by standard curve fitting (3 points).

TABLE 3

Solubility of the compound of the present invention in phosphate buffer solution (PBS, pH 7.4)

| Compound | Solubility (uM) |
| --- | --- |
| 1 | 602 uM |
| Control compound BAY-1834845 | 6.7 uM |

It can be seen from table 3 that the solubility of the preferred compound of the present invention in phosphate buffered solution (PBS, pH7.4) is 602 uM, which is better than that of the control compound BAY-1834845 (Example 11 of WO2016083433) and more advantageous and convenient for the development of subsequent oral dosage forms.

The inventors surprisingly found that the indazole derivatives of the present invention have good inhibitory effect on IRAK4 kinase activity, especially the indazole derivatives substituted at 2-position by amino alkyl. The indazole derivatives' inhibitory effect on IRAK4 kinase activity is 15 times higher than that of the control compound BAY-1834845, and inhibitory effect on THP-1 cell is twice as high as that of the control compound BAY-1834845, and the indazole derivatives have more excellent solubility. The significant improvement of activity and solubility was found through a large number of compound screening, and such improvements were innovative results obtained by the inventors of the present invention from a large number of activity screening and structure-activity relationships analysis, and they were not foreseeable by simple imagination.

The invention claimed is:

1. A compound of formula (I), or stereoisomers, tautomers or pharmaceutically acceptable salts thereof:

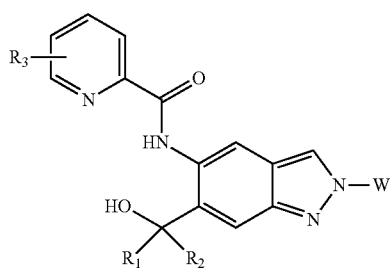

(I)

wherein:
$R_1$ and $R_2$ are independently selected from hydrogen or C$_1$-C$_6$ alkyl;
$R_3$ is selected from halogen, cyano, carboxyl, —CONR$^A$R$^B$, haloalkyl or heteroaryl; wherein the heteroaryl is optionally further substituted by one or more substituents selected from halogen, hydroxyl, cyano, carboxyl, —CONR$^A$R$^B$ or haloalkyl;
W is azetidinyl, nitrogen-containing aromatic heterocyclic ring group or nitrogen-containing aromatic heterocyclic ring group bonded via a single methylene group; wherein the azetidinyl is optionally further substituted by one or more substituents selected from —COR$^C$, —SO$_2$R$^D$, C$_1$-C$_6$ alkyl or C$_3$-C$_6$ cycloalkyl; wherein the nitrogen-containing aromatic heterocyclic ring group is optionally further substituted by one or more substituents selected from halogen, cyano, carboxyl, —CONR$^A$R$^B$ and haloalkyl;
or, W has a structure of formula (II):

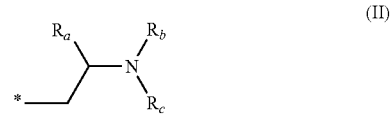

(II)

* represents bonding site of the group to rest of the molecule;
$R_a$ is selected from hydrogen, C$_1$-C$_6$ alkyl or C$_3$-C$_6$ cycloalkyl; wherein the C$_1$-C$_6$ alkyl or C$_3$-C$_6$ cycloalkyl is optionally further substituted by one or more substituents selected from halogen, hydroxyl, carboxyl and —SO$_2$NR$^E$R$^F$;
$R_b$ and $R_c$ are independently selected from hydrogen, —COR$^C$, —SO$_2$R$^D$, C$_1$-C$_6$ alkyl or C$_3$-C$_6$ cycloalkyl; or, any two of R$_a$, R$_b$ and R$_c$ together with the atoms to which they are attached form a 4-8 membered nitrogen-containing heterocyclic ring, wherein the nitrogen-containing heterocyclic ring may be further substituted by one or more oxo groups (O═);
R$^A$, R$^B$, R$^E$ and R$^F$ are independently selected from hydrogen, C$_1$-C$_6$ alkyl or C$_3$-C$_6$ cycloalkyl; wherein the alkyl or cycloalkyl is optionally further substituted by one or more substituents selected from halogen, hydroxyl, cyano or haloalkyl;
R$^C$ and R$^D$ are independently selected from C$_1$-C$_6$ alkyl or C$_3$-C$_6$ cycloalkyl; wherein the alkyl or cycloalkyl is optionally further substituted by one or more substituents selected from halogen, hydroxyl, cyano or haloalkyl.

2. The compound, or stereoisomers, tautomers or pharmaceutically acceptable salts thereof of claim 1, having the structure of formula (III):

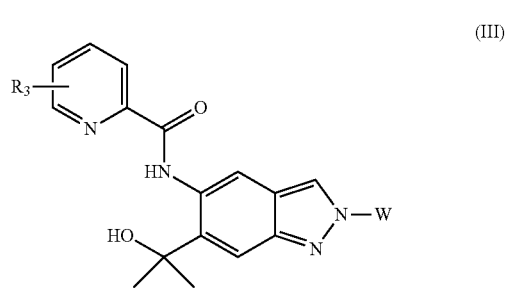

(III)

wherein R$_3$ and W are defined as in claim 1.

3. The compound, or stereoisomers, tautomers or pharmaceutically acceptable salts thereof of claim 1, having the structure of formula (IV):

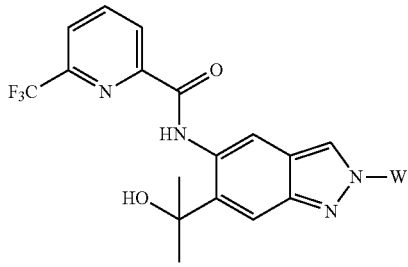

wherein, W is defined as in claim 1.

4. The compound or stereoisomers, tautomers or pharmaceutically acceptable salts thereof of claim 1, having the structure of formula (Va), (Vb) or (Vc):

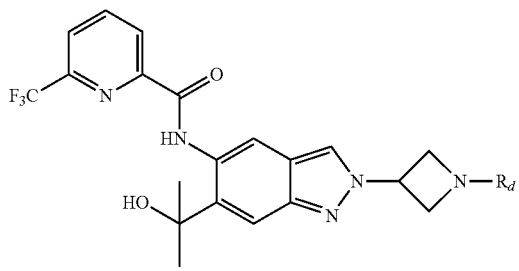

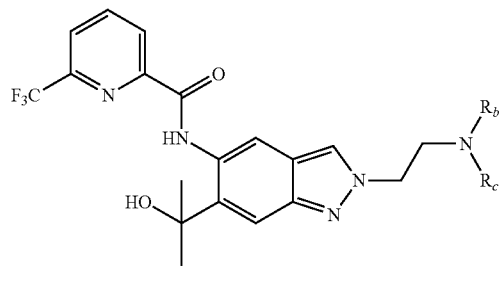

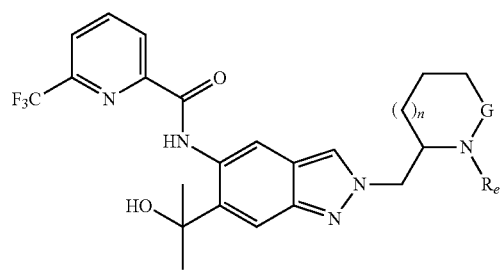

wherein:
$R_b$ and $R_c$ are defined as in claim 1;
$R_d$ and $R_e$ are independently selected from hydrogen, —$COR^C$, —$SO_2R^D$, $C_1$-$C_6$ alkyl or $C_3$-$C_6$ cycloalkyl; wherein, $R^C$ and $R^D$ are as defined in claim 1;
G is selected from —$CH_2$—, —CO— or —$SO_2$—;
n is an integer from 0 to 2.

5. The compound, or stereoisomers, tautomers or pharmaceutically acceptable salts thereof of claim 1, being N-(2-(2-(dimethylamino)ethyl)-6-(2-hydroxypropan-2-yl)-2H-indazol-5-yl)-6-(trifluoromethyl)pyridin-2-carboxamide.

6. A pharmaceutical composition comprising a therapeutically effective amount of the compound, or stereoisomers, tautomers or pharmaceutically acceptable salts thereof of claim 1, and optional pharmaceutically acceptable carriers, excipients or combinations thereof.

7. A method for inhibiting IRAK4 kinase activity, comprising administering the compound, or stereoisomers, tautomers or pharmaceutically acceptable salts thereof of claim 1 to a subject in need thereof.

8. A method for preventing or treating autoimmune diseases, inflammatory diseases or cancers by inhibiting IRAK4 kinase activity, comprising administering the compound, or stereoisomers, tautomers or pharmaceutically acceptable salts thereof of claim 1 to a subject in need thereof.

9. The compound or stereoisomers, tautomers or pharmaceutically acceptable salts thereof of claim 2, having the structure of formula (Va), (Vb) or (Vc):

-continued

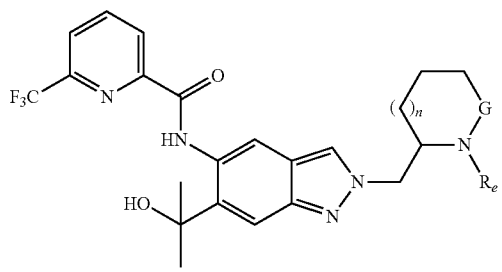

wherein:

R$_b$ and R$_c$ are defined as in claim 1;

R$_d$ and R$_e$ are independently selected from hydrogen, —COR$^C$, —SO$_2$R$^D$, C$_1$-C$_6$ alkyl or C$_3$-C$_6$ cycloalkyl; wherein, R$^C$ and R$^D$ are as defined in claim 1;

G is selected from —CH$_2$—, —CO— or —SO$_2$—;

n is an integer from 0 to 2.

10. The compound or stereoisomers, tautomers or pharmaceutically acceptable salts thereof of claim 3, having the structure of formula (Va), (Vb) or (Vc):

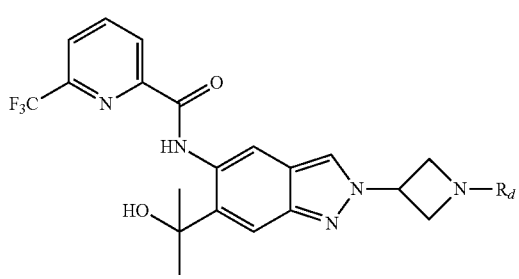

wherein:

R$_b$ and R$_c$ are defined as in claim 1;

R$_d$ and R$_e$ are independently selected from hydrogen, —COR$^C$, —SO$_2$R$^D$, C$_1$-C$_6$ alkyl or C$_3$-C$_6$ cycloalkyl; wherein, R$^C$ and R$^D$ are as defined in claim 1;

G is selected from —CH$_2$—, —CO— or —SO$_2$—;

n is an integer from 0 to 2.

11. The compound, or stereoisomers, tautomers or pharmaceutically acceptable salts thereof of claim 1, being

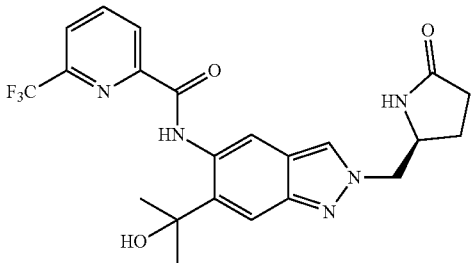

(S)—N-(6-(2-hydroxypropan-2-yl)-2-(5-oxopyrrolidin-2-yl)methyl)-2H-indazol-5-yl)-6-(trifluoromethyl)pyridin-2-carboxamide.

12. The compound, or stereoisomers, tautomers or pharmaceutically acceptable salts thereof of claim 1, being

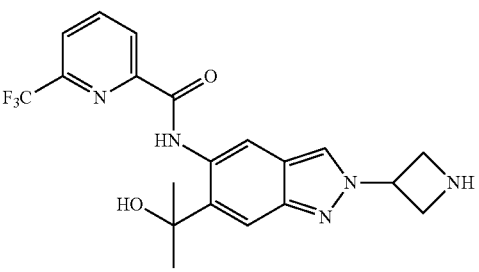

N-(2-(azetidin-3-yl)-6-(2-hydroxypropan-2-yl)-2H-indazol-5-yl)-6-(trifluoromethyl)pyridin-2-carboxamide.

13. A method for inhibiting IRAK4 kinase activity, comprising administering the pharmaceutical composition of claim 6 to a subject in need thereof.

14. A method for preventing or treating autoimmune diseases, inflammatory diseases or cancers by inhibiting IRAK4 kinase activity, comprising administering the pharmaceutical composition of claim 6 to a subject in need thereof.

15. The method of claim 8, wherein the autoimmune diseases, inflammatory diseases or cancers are selected from lymphoma, endometriosis, psoriasis, lupus erythematosus, multiple sclerosis or rheumatoid arthritis.

16. The method of claim 15, wherein the lymphoma is primary central nervous system lymphoma or diffuse large B-cell lymphoma with MYD88 L265P mutation.

17. The method of claim 14, wherein the autoimmune diseases, inflammatory diseases or cancers are selected from lymphoma, endometriosis, psoriasis, lupus erythematosus, multiple sclerosis or rheumatoid arthritis.

18. The method of claim 17, wherein the lymphoma is primary central nervous system lymphoma or diffuse large B-cell lymphoma with MYD88 L265P mutation.

* * * * *